US00PP30507P2

(12) United States Plant Patent
Tsukahara

(10) Patent No.: US PP30,507 P2
(45) Date of Patent: May 14, 2019

(54) COLEUS PLANT NAMED 'SAKCOL022'

(50) Latin Name: ***Solenostemon* sp.**
Varietal Denomination: SAKCOL022

(71) Applicant: Sakata Seed Corporation, Tsuzuki-Ku, Yokohama (JP)

(72) Inventor: Jun Tsukahara, Kakegawa Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/732,582

(22) Filed: Nov. 29, 2017

(51) Int. Cl.
*A01H 5/12* (2018.01)
*A01H 5/02* (2018.01)

(52) U.S. Cl.
USPC ..... Plt./469

(58) Field of Classification Search
USPC ..... Plt./373, 469
CPC ..... A01H 5/12; A01H 5/02
See application file for complete search history.

*Primary Examiner* — Keith O. Robinson
(74) *Attorney, Agent, or Firm* — Bethany Reid Roahrig; Cochran Freund & Young LLC

(57) ABSTRACT

A coleus plant particularly distinguished by small leaves having a pink and dark burgundy inner leaf color and green margins, is disclosed.

3 Drawing Sheets

Genus and species: *Solenostemon* sp.
Variety denomination: 'SAKCOL022'.

BACKGROUND OF THE NEW PLANT

The present invention comprises a new and distinct variety of coleus, botanically known as *Solenostemon* sp., and hereinafter referred to by the variety name 'SAKCOL022'.

'SAKCOL022' originated from the open pollination of 8 unpatented proprietary lines crossed pollinated in October 2014 in Kakegawa, Japan. The breeder put breeding materials '14P-202', '14P-203', '14P-205', '14P-210', '14P-211', '14P-212', '14F-19', and '14F-20-2' in a cage. Bees then crossed them at random. The breeder harvested 1,200 seeds from '14P-211'. These seeds were composed of hybrid seeds and self-pollinated seeds.

The seeds obtained from the '14P-211' plant were sown and a single plant selection designated 'L2015-CO372' was selected for its multi-colored leaf pattern with a pink and dark burgundy inner leaf color and green margins with mounding plant habit with small leaves. The breeder confirmed that 'L2015-CO372' was fixed and stable. 'L2015-CO372' was subsequently named 'SAKCOL022'.

The new plant was first asexually propagated from October 2015 to April 2016 in Japan and has been asexually reproduced by vegetative cuttings for almost three years in Japan. The present invention has been found to retain its distinctive characteristics through successive asexual propagations by vegetative cuttings.

'SAKCOL022' has not been made publicly available or sold more than one year prior to the filing date of this application.

SUMMARY OF THE NEW PLANT

The following are the most outstanding and distinguishing characteristics of the new variety when grown under normal horticultural practices in Salinas, Calif.

1. Small leaves; and
2. Pink and dark burgundy inner leaf color and green margins.

DESCRIPTION OF THE PHOTOGRAPHS

This new coleus plant is illustrated by the accompanying photographs which show the overall plant habit, foliage, and flowers of a plant aged 3 months old. The colors are as true as can be reasonably obtained by conventional photographic procedures.

Figure 1:
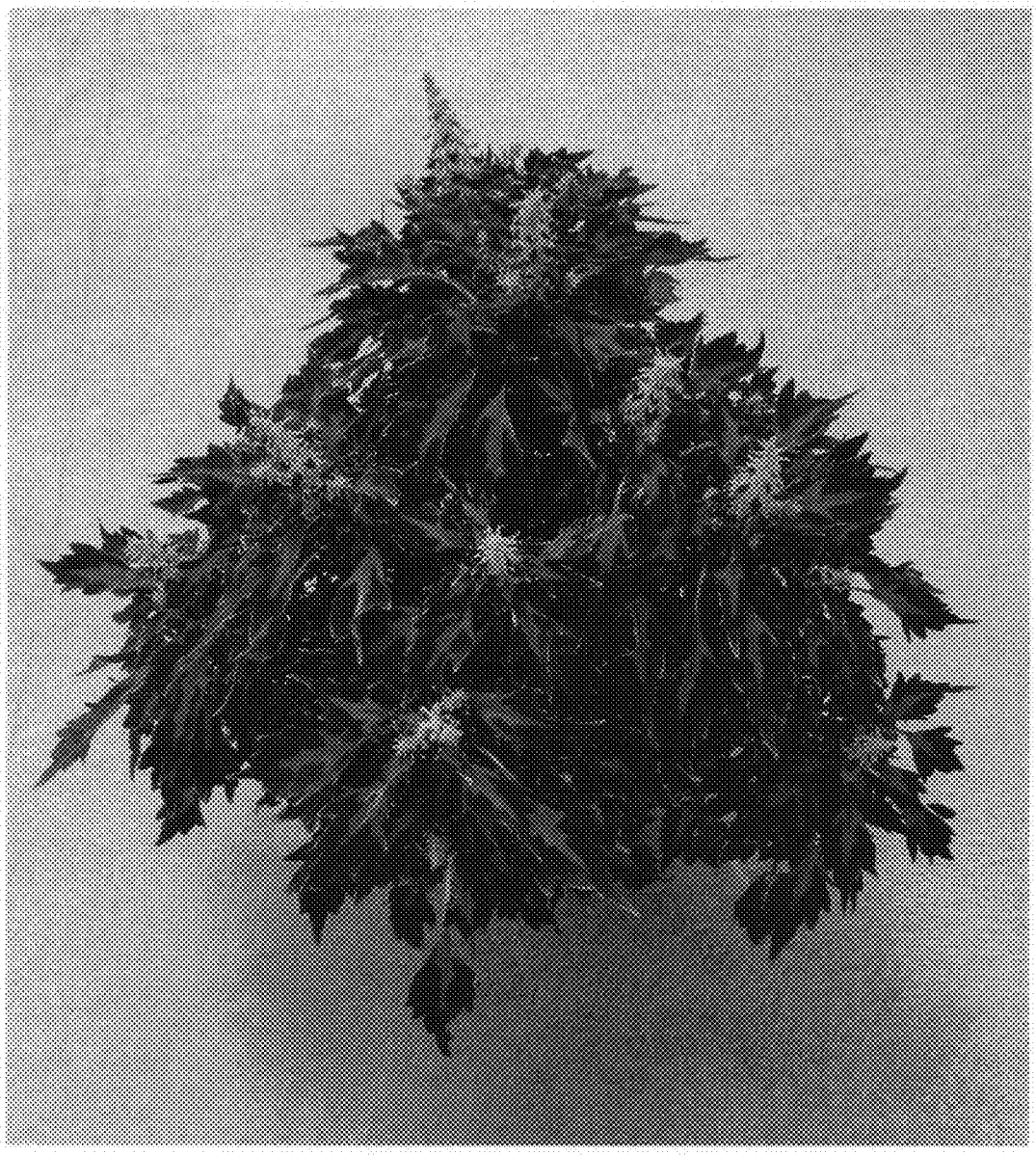
Figure 2:
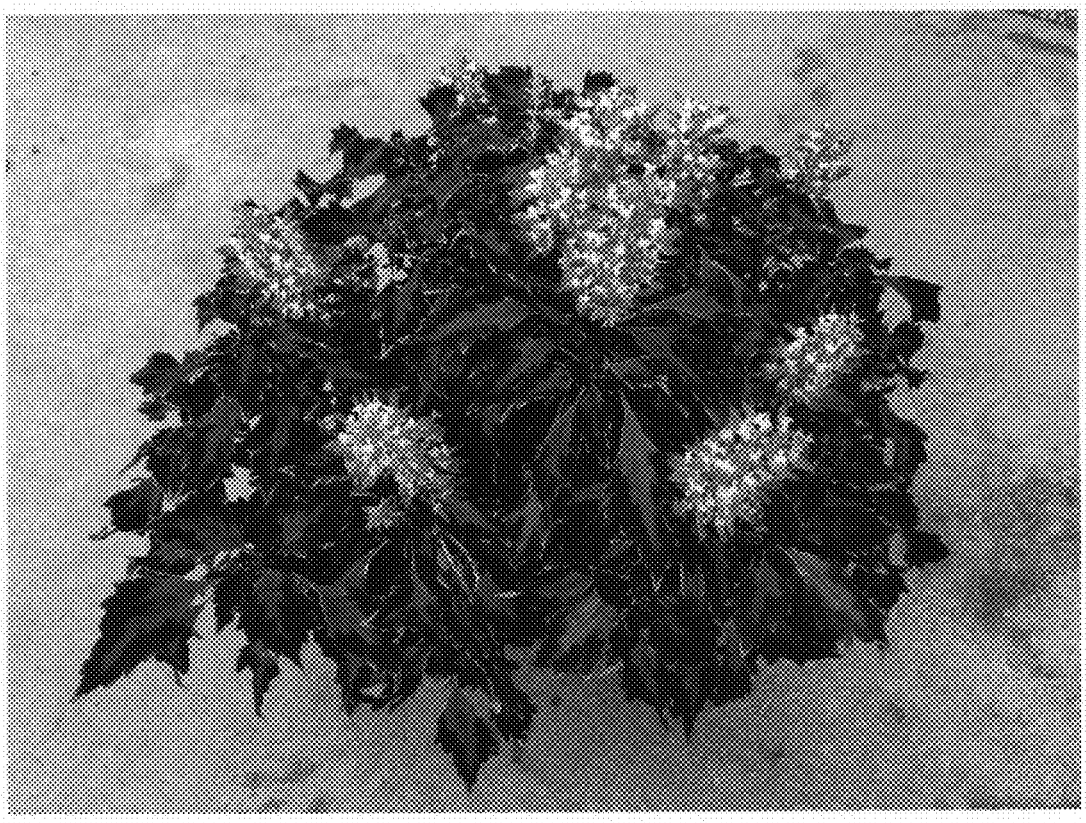
Figure 3:
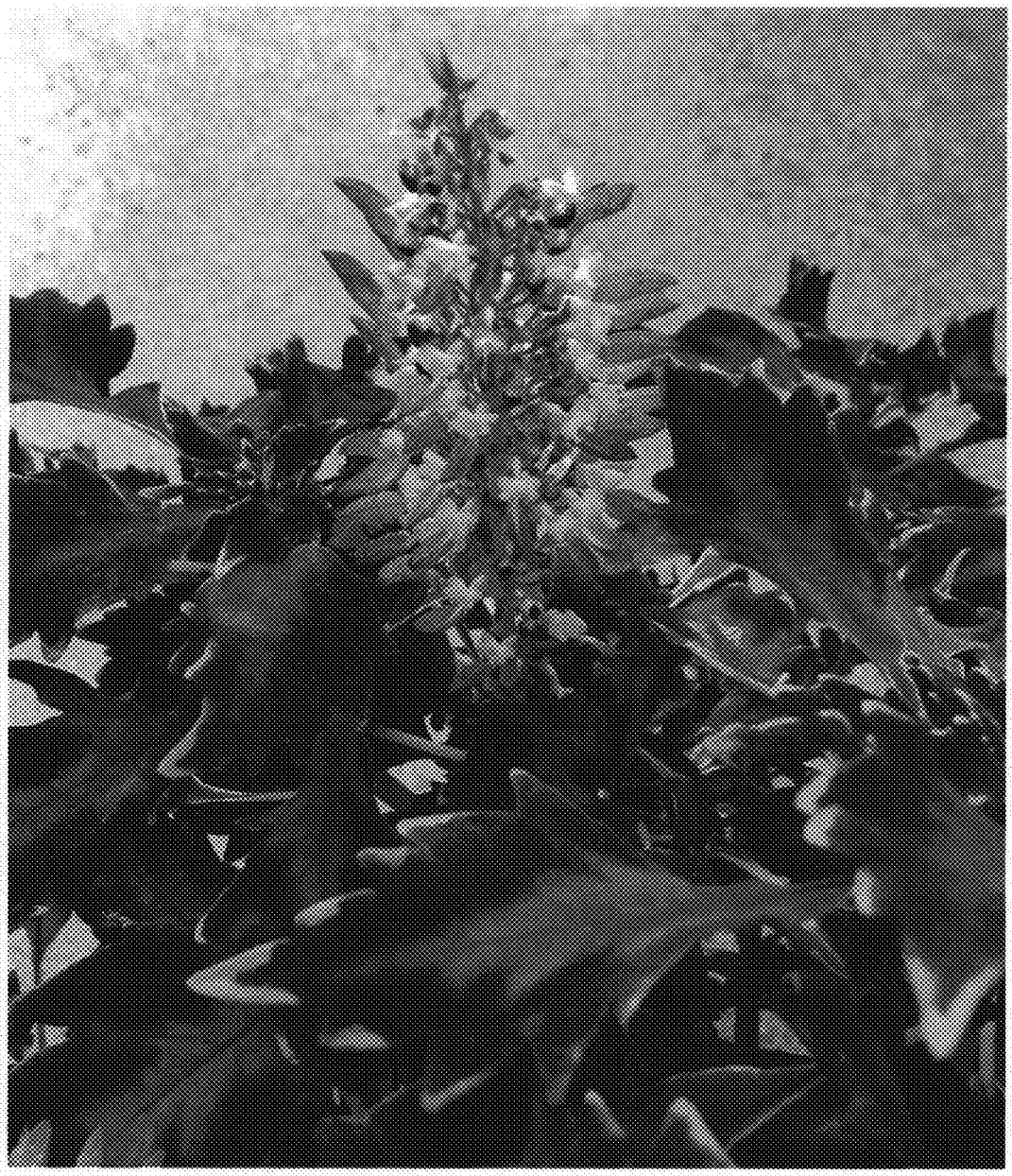

FIG. 1 shows the overall plant habit and foliage.
FIG. 2 shows the overall plant habit and foliage in flower.
FIG. 3 shows a close up of a flowering stalk and foliage.

DESCRIPTION OF THE NEW VARIETY

The following detailed descriptions set forth the distinctive characteristics of 'SAKCOL022'. The data which defines these characteristics were collected from plants grown three months from transplant into 4-inch pots from rooted cuttings in Salinas, Calif., under greenhouse conditions. Color references are to The Royal Horticultural Society Colour Chart, $4^{th}$ edition. Anatomic labels are from *The Cambridge Illustrated Glossary of Botanical Terms*, by M. Hickey and C. King, Cambridge University Press.

Classification:
*Family*.—Lamiaceae.
*Botanical name*.—*Solenostemon* sp.
*Common name*.—Coleus.
*Denomination*.—'SAKCOL022'.

Plant:
*Type*.—Annual.
*Habit*.—Compact.
*Form*.—Compact and dense, 4 main branches.
*Height*.—33.0 cm.
*Spread*.—42.0 cm.
*Propagation type*.—Vegetative cuttings.

Environmental conditions for plant growth: The terminal 1.0 to 1.5 inches of an actively growing stem was excised. The vegetative cuttings were propagated for five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24 degrees C.

Lateral branches:

*Length.*—10.0 cm to 18.0 cm.

*Diameter.*—0.7 cm to 1.0 cm.

*Internode length.*—1.0 cm to 1.5 cm.

*Strength.*—Branches separate easily.

*Aspect.*—Long, trailing to semi-trailing.

*Shape in cross-section.*—Circular.

*Texture.*—Dull, very slight pubescent.

*Pubescence color.*—RHS N155A (White).

*Stem/branch color.*—Closest to RHS 145C (Yellow-Green).

*Flowering branch.*—Present, very slight pubescence.

Leaves:

*Arrangement.*—Opposite.

*Length.*—6.8 cm.

*Width.*—3.5 cm.

*Broadest part of the leaf blade.*—Middle.

*Shape.*—Pinnatipartite.

*Apex.*—Caudate.

*Base.*—Acuminate.

*Margin.*—Sinuate.

*Texture, upper surface.*—Dull, very slight pubescence.

*Texture, lower surface.*—Glabrous with pronounced venation.

*Venation pattern.*—Pinnate.

*Vein color, upper surface.*—RHS N186A (Greyed-Purple).

*Vein color, lower surface.*—Closest to RHS 196A (Greyed-Purple).

*Petiole length.*—3.4 cm.

*Petiole diameter.*—2.0 mm.

*Petiole color.*—Closest to but lighter than RHS 1C (Green-Yellow) with RHS 59A towards leaf base.

*Petiole texture.*—Very slight pubescent.

*Variegation.*—Present.

*Leaf color.*—Multicolored, hot pink at center with dark maroon towards leaf margin, and green at margin. Upper surface: RHS 59B (Red-Purple) with closest to but darker than RHS 200A (Brown) increasing towards margin RHS 143A (Green) at margin. Lower surface: RHS 138B (Green) with blotches of RHS 61A (Red-Purple) increasing towards midpoint with very slight RHS 159D (Orange-White) close to venation and very small blotches of RHS 187A (Greyed-Purple) throughout.

Flowers: Terminal flower stalk observed having multiple buds and forming a cone shape.

*Stalk length.*—9.5 cm.

*Stalk diameter.*—3.5 cm.

*Stalk color.*—Closest to RHS 144B (Yellow-Green).

*Flower color.*—RHS 93B (Violet-Blue) with RHS N155A (White) at base.

Temperature tolerance: 2 degrees C. to 35 degrees C.

Disease or insect resistance: No disease or insect resistance observed.

COMPARISON WITH PARENTAL LINES AND KNOWN VARIETY

'SAKCOL022' is a new and distinct cultivar of coleus owning to its unique multicolored leaf pattern and mounding plant habit and small leaves. It is distinguished from its parents as described in Table 1 below.

TABLE 1

| Comparison with Parental Lines | | |
|---|---|---|
| | Leaf color | Leaf size |
| Parental lines | | |
| '14P-202' | Brown | Extremely small |
| '14P-203' | Rose and green | Extremely small |
| '14P-205' | Brown | Extremely small |
| '14P-210' | Rose and brown | Small |
| '14P-211' | Rose and green | Small |
| '14P-212 | Rose, brown and green | Large |
| '14F-19' | Dark brown and green | Medium |
| '14F-20-2' | Rose, brown and green | Extremely large |
| Comparison | | |
| 'SAKCOL022' | RHS 59B (Red-Purple) with closest to but darker than RHA 200A (Brown) increasing towards margin, RHS 143A (Green) | Extremely small<br>Length: 6.8 cm<br>Width: 3.5 cm |

| | Leaf shape | Leaf margin | Plant habit |
|---|---|---|---|
| Parental lines | | | |
| '14P-202' | Orbicular | Crenate | Creeping |
| '14P-203' | Orbicular | Crenate | Creeping |
| '14P-205' | Orbicular | Crenate | Creeping |
| '14P-210' | Ellipse | Serrate | Mounding |
| '14P-211' | Ellipse | Serrate | Mounding |
| '14P-212 | Ovate | Crenate | Erect |
| '14F-19' | Ovate | Crenate | Erect |
| '14F-20-2' | Orbicular | Crenate | Erect |
| Comparison | | | |
| 'SAKCOL022' | Pinnatipartite | Sinuate | Mounding |

'SAKCOL022' is most similar to the commercial variety PARTY TIME 'Pink Berry', also known as 'SAKCOL018' (U.S. Plant Pat. No. 28,823), however, there are differences as listed in Table 2 below.

TABLE 2

| Comparison with Similar Variety | | |
|---|---|---|
| Characteristic | 'SAKCOL022' | 'PARTY TIME 'Pink Berry' |
| Leaf color, upper surface | RHS 59B (Red-Purple) with closest to but darker than RHS 200A (Brown) increasing towards margin RHS 143A (Green) at margin | Closest to RHS 59C (Red-Purple) with blotches closest to RHS 200A (Black) with slight RHS 147A (Green) increasing towards margin, and RHS 143A (Yellow-Green) at leaf margin. |
| Leaf color, lower surface | RHS 138B (Green) with blotches of RHS 61A (Red-Purple) increasing towards midpoint with very slight RHS 159D (Orange-White) close to venation and very small blotches of RHS 187A (Greyed-Purple) throughout | Closest to RHS147B (Yellow-Green) with blotches of RHS 59A (Red-Purple) towards mid vein with most mature foliage having a blotch closest to RHS 27A (Orange) at base |
| Plant growth habit | Compact, Mounding | Compact, Semi-creeping |

I claim:

1. A new and distinct variety of coleus plant named 'SAKCOL022' as illustrated and described herein.

* * * * *